United States Patent [19]

Johnson

[11] Patent Number: 5,683,707
[45] Date of Patent: Nov. 4, 1997

[54] BIOSTATIC MEDIA FOR ACTIVE AGENTS

[76] Inventor: Richard R. Johnson, 980 Camden, Aurora, Ill. 60504

[21] Appl. No.: 493,584

[22] Filed: Jun. 22, 1995

Related U.S. Application Data

[63] Continuation of Ser. No. 240,961, May 9, 1994, abandoned, which is a continuation of Ser. No. 974,527, Nov. 12, 1992, abandoned.

[51] Int. Cl.$^6$ .................................................. A01N 25/24
[52] U.S. Cl. ...................... 424/407; 424/405; 424/76.5; 424/76.6; 424/76.8; 424/684; 514/63
[58] Field of Search .......................... 424/407, 405, 424/76.3, 76.4–76.9, 709, 489, 493, 499, 421, 684, 724; 574/63; 423/327, 328

[56] References Cited

U.S. PATENT DOCUMENTS

| | | | |
|---|---|---|---|
| 1,583,154 | 5/1926 | Howard | 424/704 |
| 3,449,492 | 6/1969 | Jensen | 424/684 |
| 5,135,740 | 8/1992 | Katz et al. | 424/401 |
| 5,140,949 | 8/1992 | Chu et al. | 119/174 |
| 5,230,893 | 7/1993 | Gotou et al. | 424/409 |

FOREIGN PATENT DOCUMENTS

| | | | |
|---|---|---|---|
| 0270129 | 6/1988 | European Pat. Off. | |
| 2352265 | 4/1975 | Germany | 424/684 |
| 1171555 | 7/1989 | Japan | 424/76.1 |
| 2252968 | 8/1992 | United Kingdom | 424/76.1 |

Primary Examiner—Neil S. Levy
Attorney, Agent, or Firm—Patrick N. Burkhart; Anne K. Burkhart

[57] ABSTRACT

Liquid and powdered media for active ingredients, and specifically biostatic substrates or bases for the application of anti-microbial compositions, insecticides, and the like. In one embodiment, the present invention provides a composition for use as a substrate that includes powdered clinoptilolite in solution, polyethelenimine in solution, glycerol in solution, and starch in solution. Ingredients such as anti-microbial compounds, insecticides, and/or fragrances can be added to the substrate. In another embodiment, a synthetic zeolite can be substituted for the powdered clinoptilolite. The present invention also provides several methods for making liquid and powdered media, and a method and apparatus for controlling the emission of bacterial odors from a volume of material. Also disclosed are compositions that act as a compatible base or substrate for anti-microbial and other solutions. The present invention provides a safer and more ecologically benign method for anti-microbial applications and enhances the effective life of certain anti-microbials, thus providing a time-released and residual quality unattainable with known water-diluted or solvent-based anti-microbials.

8 Claims, 1 Drawing Sheet

BIOSTATIC MEDIA FOR ACTIVE AGENTS

This is a continuation of application Ser. No. 08/240,961, filed on 9 May, 1994, now abandoned, which was a continuation of Ser. No. 07/974,527, filed on 12 Nov. 1992, now abandoned.

TECHNICAL FIELD

The present invention relates to liquid and powdered biostatic media for active ingredients, and specifically to biostatic substrates or bases for the application of anti-microbial compositions, insecticides, and the like.

BACKGROUND OF THE INVENTION

Irregular surfaces provide an ideal environment for the proliferation of a variety of microbial populations or colonies. Over the years there have been many attempts to apply anti-microbial formulations to worn, eroded, or otherwise irregular surfaces, with the desired result ranging from control of mold, mildew, or fungi to the abatement of disturbing odors caused by the presence of various forms of bacteria.

Unfortunately, the actual result of such applications frequently is inadequate. Anti-microbial solutions in liquid formulas are typically water based and, due to the potentially harmful properties of the anti-microbial compounds, must be very diluted at final use concentrations. Such solutions evaporate rapidly when applied safely in these "at use" dilutions. The swift evaporation of an anti-microbial hastens its useful life, and decreases its ability to perform.

In addition to water-based anti-microbials, solvent-based anti-microbials have also been used. Solvent-based anti-microbials share the evaporation problems of known water-based anti-microbials, and further present environmental threats due to the properties of the solvents themselves.

Even after known anti-microbials have been applied, the nature of rough, porous surfaces often allows unwelcome microbes to advance quickly, without restraint from dormancy. Inconsistent surface contact, minimal dwell time of the anti-microbial due to evaporation, and unrestricted pathways allow the microbes to colonize quickly, sometimes increasing to greater numbers than before the anti-microbial was applied. This phenomenon may be due to the colonization/cluster formation of many types of microbes. When bonded tightly together, colonies grow more slowly. When the anti-microbial is applied, the outer layers of colonies die, the inner layers can break loose and move about freely. Thus, after the anti-microbial evaporates, the inner layers of the microbe colony increase their numbers, sometimes quickly surpassing the pre-application colony size.

In addition to the difficulties enumerated above, many known anti-microbial compounds require complex and dangerous solvent-based medium/substrate formulations, and the anti-microbial compounds themselves are potentially harmful to users and/or the environment.

As can be seen from the foregoing, presently known anti-microbial application media and techniques are not only complex and potentially dangerous, but often result in a substantial increase in undesirable microbial population. It can be seen that the need exists for a safe, simple medium for the application of anti-microbials and the like that will not only serve to kill microbial colonies on contact, but prevent their post-application proliferation.

SUMMARY OF THE INVENTION

The present invention provides liquid and powdered media for active ingredients, and specifically biostatic substrates or bases for the application of anti-microbial compositions, insecticides, and the like. In one embodiment, the present invention provides a composition for use as a substrate that includes powdered clinoptilolite in solution, polyethelenimine in solution, glycerol in solution, and starch in solution. Ingredients such as anti-microbial compounds, insecticides, and/or fragrances can be added to the substrate. In another embodiment, a synthetic zeolite can be substituted for the powdered clinoptilolite.

The present invention also provides several methods for making liquid and powdered media, and a method and apparatus for controlling the emission of bacterial odors from a volume of material.

The present invention provides water-soluble compositions that act as a compatible base or substrate for anti-microbial and other solutions. The present invention enhances the effective life of certain anti-microbials, thus providing a time-released and residual quality unattainable with known water-diluted anti-microbials.

The compositions of the present invention adhere to and increase the surface area contacted by the anti-microbial solution, due to their ability to expand and swell. In combination, these properties prove to be synergistically significant as an odor-reducing biocidal, and are especially efficacious when applied to porous surfaces and surfaces with cracks and crevices where bacteria, fungi, & mold hide in a dormant state. The formulations' swelling action increases contact time with microbes.

The compositions impede and in some cases prohibit the flow of oxidated air, thus effectively killing existing microbes and cutting off the pathways for microbial proliferation. When the formulation dries, it leaves behind a durable yet malleable blanketed filmy, anti-microbial residue. The presence of the filmy residue further inhibits the ability of microbes to thrive and grow, as they will likely contact and succumb to the anti-microbial which inhabits within the filmy/residue left behind. Although the composition itself is water soluble, the filming residue is significantly water resistant, and can be removed only with water and mild abrasion.

Other objects and advantages of the present invention will be apparent upon reference to the accompanying description when taken in conjunction with the following drawing.

DETAILED DESCRIPTION OF THE PREFERRED EMBODIMENTS

Figure 1:
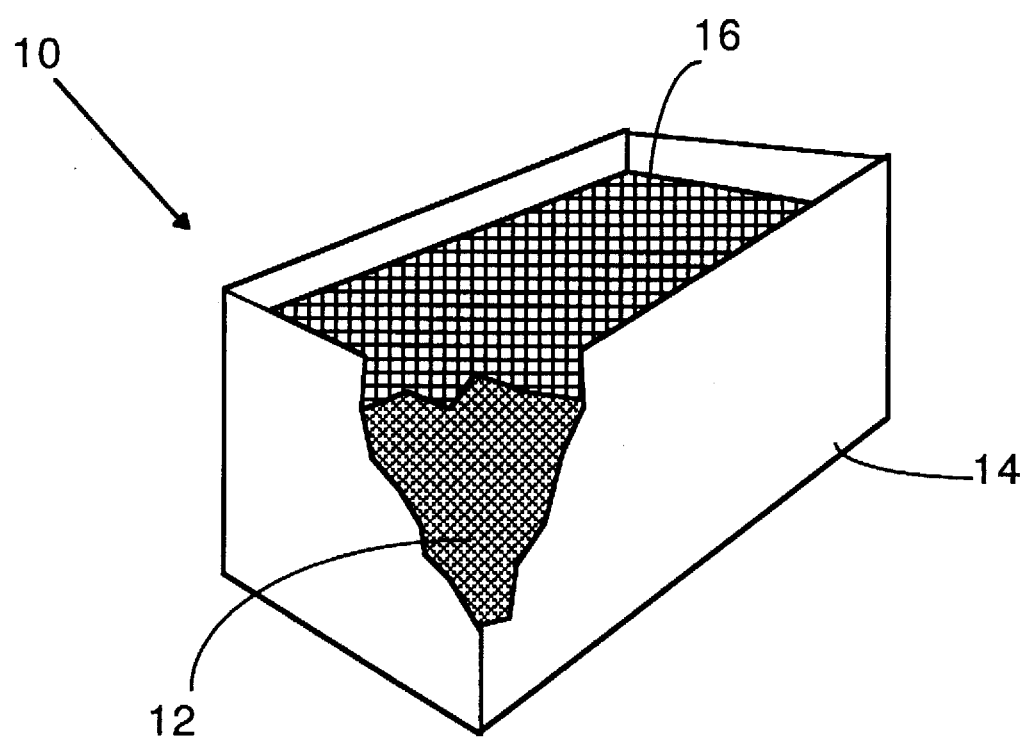
FIG. 1 illustrates a schematic perspective view of an apparatus for controlling the emission of bacterial odors from a volume of material employing the principles of the present invention.

In the illustrated embodiments, the compositions of the present invention include a mixture of four principal components, designated (A), (B), (C), and (D) as follows:

Component A is cationic Clinoptilolite, $Na_6[Al_6Si_{30}O_{72}]\ 24H_2O$, crushed to a powder size approximately 325 Tylermesh, 44 um.

Component B is polyethylenimine, $(C2H5N)x$ (x=900–1400), a polymer substance used for fine-coating surfaces and enhancing surface adhesion.

Component C is glycerol, a $CH_2OHCHOHCH_2OH$ low volatile plasticizer, which allows the other components to diffuse within the coating applications and increases the surface contact of the composition.

Component D is starch, mildly soluble, is used to thicken the filmy substance left in the uneven surfaces, as described hereinbelow.

Powder Grade Clinoptilolite is naturally electronegative, and will therefore chemically combine more readily with the polymer polyethylenimine which is cationic. The high lattice structure of clinoptilolite is well suited to store ammonium compounds. Over time, it will purge itself of these compounds, providing the time release attributes of the compositions of the present invention.

Starches such as Industrial Grade corn starch are soluble in water. When starches dry, they leave behind a residue. Also, as it dries, it swells. This swelling increases the surface area of the composition and increases its effectiveness. Also assist in gelling in polymerization and plasticization.

Glycerol thickens the composition and causes more adhesion to the surface when initially applied.

Polyethylenimine is a polymer, and serves as an adhesive bonding agent for the composition. Polyethelenimine enhances the ability of the composition to leave behind a thin film after the composition has been applied to a surface and dried.

Compositions made from these components are water-soluble, and have been found to be extremely biostatic. Tests have shown the filmy residue left behind after the compositions dry to be water-resistant, durable, and malleable. Tests also show the composition and film to exhibit excellent surface adhesion, odor reduction abilities, time-release attributes, and persons filling abilities.

EXAMPLE I

The components set forth above can be combined in the following proportions to provide a time-released base/substrate for active ingredients.

A. 2–50 g/liter aqueous solution
B. 1–30% in solution of 33% PEI
C. 1–30% in solution
D. 5–60 g/liter aqueous solution

EXAMPLE II

The components set forth above can also be combined in the following proportions to provide a time-released base/substrate for active ingredients. This formulation represents the best mode of practicing the invention currently contemplated by the inventor.

A. 2–5 g/liter aqueous solution
B. 1–3% in solution of 33% PEI
C. 1–3% in solution
D. 5–10 g/liter aqueous solution This formulation can be advantageously used as a medium for anti-microbial agents. The preferred anti-microbial is a dual quaternary ammonium, which offers excellent biocidal characteristics and is relatively safe, both environmentally and to users.

EXAMPLE III

Reducing the amount of component B results in a substrate that is slightly less thick, and thus more suitable for uses requiring less viscosity. Substrates according to this example can be fabricated using the following formula:

A. Powdered clinoptilolite in an aqueous solution of 2 to 5 grams per liter;
B. 0% to 1.5% polyethelenimine in solution;
C. 1% to 3% glycerol in solution; and
D. Starch in an aqueous solution of 5 to 10 grams per liter.

As with the formula in Example I, this formulation provides an excellent medium for antimicrobial compounds, insecticides, fragrances, and other active agents.

METHODS OF MAKING

The inventor has developed several methods for making biostatic compositions, each of which offers distinct advantages.

METHOD I

After components A,B,C, and D, along with a quaternary ammonium compound, have been mixed at a room temperature of 68–72 degrees F., the mixture is heated to a vigorous boil. Once the solution begins to rise, heat is stopped instantly, since heating past this point could have an adverse affect on the quaternary ammonium compound. Heating the mixture serves to set the particles in suspension and thicken the mixture. The substrate produced by this method displays a significant increase in the tightness of the dried, applied substrate.

METHOD II

In this method, the boiling process described in Method I is effected only on a mixture of components A, B, C, and D, without the anti-microbial. Once the mixture is allowed to cool to room temperature, it can be stored for an indefinite period. An anti-microbial or pesticide agent can be added to the mixture just prior to use. This method eliminates any concerns regarding the potential effect of the boiling process on the pesticide or anti-microbial.

METHOD III

First, components B, C, and D are mixed according to the preferred formula. Heat is applied to the mixture to bring the mixture to a slightly elevated viscosity, and the mixture is allowed to cool.

Next, component A is impregnated with a concentrated quaternary ammonium solution, at room temperature. This clino/quats mixture is then set aside until the quaternary ammonium compound has reached a point of maximum sorption in the clinoptilolite powder. Typically, clinoptilolite will absorb 15–20% of its own weight. Optionally, heating the quats concentrate to approximately 150 degrees F. has been found to facilitate the impregnation process, in which case the clino/quats mixture should be allowed to cool to room temperature before proceeding with the next step.

Finally, the impregnated clino/quats concentrate is mixed into the cooled B, C, and D solution at a concentration of approximately 1000 ppm of clino/quats.

The impregnation of component A with quaternary ammoniums produces a synergistic residual cidal effect, as it extends the cidal life of the quats dramatically. This effect is created two ways. First, the quats are time released as described above. secondly, the anti-microbial, when impregnated in the clinoptilolite, has a zone of inhibition of 0.5–2 mm. These qualities greatly enhance the ability of the composition to prohibit the colonization/cluster regeneration of microbial populations.

METHOD IV

The formulas can vary according to the desired sensitivity to moisture in the end-use product. The product can be made significantly water resistant or highly soluble in water by varying the proportion of component B, C, and D. Making the product more sensitive to water tends to enhance the cidal effect on microbes. The metabolic activity of microbes is such that they emit moisture. Thus the microbes proliferate and emit increasing levels of moisture, they will "sink into", or become surrounded by, the filmy residue. By making the product more water resistant, the product can adhere to surfaces even under moist to wet conditions.

METHOD V

Extra levels of component A may be added to the composition for high odor applications. Additional amounts of component A should be added to a final mixture, and not impregnated with the quats material. Component A has been found to readily absorb gaseous organic by-products which are given off by decaying organic matter. Consequently, after the microbes have been killed, the composition can absorb the odors from their decay.

METHOD VI

Synthetic Zeolites may be used in place of the component A when the surface to be treated is extremely porous, for example, surfaces with holes of approximately 40–200 tyler mesh size. The synthetic zeolites have a more consistent lattice structure than clinoptilolites, and would thus work well on surfaces such as crawl spaces, carpets, outdoor matting, and artificial turf.

METHOD VII

In this method, components A, B, C, D, and an anti-microbial are mixed at room temperature, the allowed to separate into a slurry-like residue below a liquid the liquid is removed, and the remaining residue is allowed to dry into a powder. The powder is highly concentrated, and can be used in any situations where powders would work better than liquids. Such situations include, for example, skin and foot medical applications, carpet powder, and so on. It is also contemplated that the powder could be mixed with glycerol to provide a time-release biocidal salve.

In addition to those referenced above, the present invention is well-suited to a variety of other uses, for example, as an anti-mold wall paper paste, or a wall paint base mix. The present invention is also useful as a base for pesticidal applications, for the same reasons as mentioned above. The present invention is contemplated to enable a reduction in the amount of pesticidal agent, due to its adhesion and time-release properties. These properties increase the safety of pesticides from an environmental standpoint and for household use.

An illustrative embodiment of an apparatus 10 for controlling the emission of bacterial odors from a volume of material 12 is shown in FIG. 1. The material 12, which may, for example, be compost material, sewage waste material, or some other bacteria-containing substance, is held in a container 14. The material 12 is covered with a gas-permeable membrane 16, which may, for example, be provided as a sheet of mesh material, textile material, or the like. The membrane 16 is coated or impregnated with an anti-microbial composition, as described hereinabove, such as with a mixture of powdered clinoptilolite in solution, polyethelenimine in solution, glycerol in solution, starch in solution, and an anti-microbial agent such as a quaternary ammonium compound.

As odiferous, bacteria-laden gas diffuses from the material 12, it passes through the membrane 16, where the anti-microbial substrate kills bacteria and absorbs odors. The substrate may be replenished from time to time simply by applying additional substrate material to the membrane, for example, by spraying.

Although the present invention has been described with reference to specific embodiments, those of skill in the art will recognize that changes may be made thereto without departing from the scope and spirit of the invention as set forth in the appended claims.

I claim as my invention:

1. A composition comprising:

an aqueous solution of powdered clinoptilolite at a concentration of 2–5 g of powdered clinoptilolite per liter of aqueous solution;

an aqueous solution of 33% polyethelenimine at a concentration of 1–30% in solution;

an aqueous solution of glycerol at a concentration of 1–30% in solution; and an aqueous solution of starch at a concentration of 15–60 grams of starch per liter of aqueous solution.

2. A composition comprising:

powdered clinoptilolite in an aqueous solution at a concentration level of 2 to 5 grams of powdered clinoptilolite per liter of aqueous solution;

1% to 3% polyethelenimine in solution;

1% to 3% glycerol in solution; and starch in an aqueous solution at a concentration level of 5 to 10 grams of starch per liter of aqueous solution.

3. A composition according to claim 2, wherein said clinoptilolite has a powder size of approximately 325 Tyler-mesh.

4. A composition according to claim 2, further comprising an anti-microbial agent.

5. A composition according to claim 2, wherein said anti-microbial agent comprises a quaternary ammonium compound.

6. A composition according to claim 2, further comprising a fragrance agent.

7. A composition according to claim 2, further comprising an insecticidal agent.

8. A composition comprising:

powdered clinoptilolite in an aqueous solution at a concentration level of 2 to 5 grams of powdered clinoptilolite per liter of aqueous solution;

0% to 1.5% polyethelenimine in solution;

1% to 3% glycerol in solution;

an anti-microbial compound; and starch in an aqueous solution at a concentration level of 5 to 10 grams of starch per liter of aqueous solution.

* * * * *